(12) United States Patent
Steiner et al.

(10) Patent No.: US 11,536,704 B2
(45) Date of Patent: Dec. 27, 2022

(54) PRODUCING A HOLE IN A BIRD EGG FOR DETERMINING THE SEX OF THE BIRD EGG

(71) Applicant: TECHNISCHE UNIVERSITAET DRESDEN, Dresden (DE)

(72) Inventors: Gerald Steiner, Schwarzenberg (DE); Grit Preusse, Radebeul (DE); Edmund Koch, Dresden (DE); Roberta Galli, Dresden (DE); Christian Schnabel, Dresden (DE)

(73) Assignee: TECHNISCHE UNIVERSITÄT DRESDEN, Dresden (DE)

( * ) Notice: Subject to any disclaimer, the term of this patent is extended or adjusted under 35 U.S.C. 154(b) by 915 days.

(21) Appl. No.: 16/344,988

(22) PCT Filed: Oct. 26, 2017

(86) PCT No.: PCT/EP2017/077507
§ 371 (c)(1),
(2) Date: Jun. 24, 2019

(87) PCT Pub. No.: WO2018/078046
PCT Pub. Date: May 3, 2018

(65) Prior Publication Data
US 2019/0339244 A1    Nov. 7, 2019

(30) Foreign Application Priority Data
Oct. 26, 2016    (DE) ..................... 10 2016 013 155.1

(51) Int. Cl.
*G01N 33/08*    (2006.01)
*A01K 45/00*    (2006.01)
(Continued)

(52) U.S. Cl.
CPC ............. *G01N 33/08* (2013.01); *A01K 43/00* (2013.01); *A01K 45/007* (2013.01);
(Continued)

(58) Field of Classification Search
CPC ...... A01K 43/00; A01K 45/007; G01N 33/08; G01N 21/6486; G01N 21/65; G01N 33/483
See application file for complete search history.

(56) References Cited

U.S. PATENT DOCUMENTS 9,835,560 B2    12/2017 Galli
10,458,967 B2 *  10/2019 Hurlin ................. G01N 33/085
(Continued)

FOREIGN PATENT DOCUMENTS

DE    10 2014 010 150    1/2016
DE    10 2016 004 051    7/2017
(Continued)

OTHER PUBLICATIONS

PCT Search Report and IPER in PCT/EP2017/077507.
(Continued)

*Primary Examiner* — Michael McCullough
*Assistant Examiner* — Jessica L Burkman
(74) *Attorney, Agent, or Firm* — Greenblum & Bernstein, P.L.C.

(57) ABSTRACT

To determine the sex of a bird egg, a hole is produced at the blunt end of the bird egg, wherein the hole affects the calcareous shell and the outer shell membrane, whereas the inner shell membrane remains intact. In the region of the hole at the blunt end, beneath the intact inner shell membrane, at least one blood vessel is registered and the blood therein is excited by means of a preset incident radiation, the back-scattered radiation of which blood is measured, detected and evaluated for the sex determination.

7 Claims, 7 Drawing Sheets

(51) Int. Cl.
    *G01N 21/64*     (2006.01)
    *A01K 43/00*     (2006.01)
    *G01N 21/65*     (2006.01)
    *G01N 33/483*     (2006.01)

(52) U.S. Cl.
    CPC ......... *G01N 21/6486* (2013.01); *G01N 21/65* (2013.01); *G01N 33/483* (2013.01)

(56) References Cited

U.S. PATENT DOCUMENTS

| | | | |
|---|---|---|---|
| 10,477,841 B2 * | 11/2019 | Vishnia | A01K 41/023 |
| 2014/0158050 A1 | 6/2014 | Grajcar | |

FOREIGN PATENT DOCUMENTS

| | | |
|---|---|---|
| DE | 10 2016 005 974 | 11/2017 |
| JP | 64-55131 | 3/1989 |
| WO | 2017/017277 | 2/2017 |
| WO | 2017/174337 | 10/2017 |

OTHER PUBLICATIONS

German Office Action issued in German Application No. 10 2016 013 155.

Article entitled In Ovo Sexing of Domestic Chicken Eggs by Raman Spectroscopy by R. Galli et al., Aug. 2016.

Atricle entitled Egg Handling and Storage by J. Brake et al., 1997.

* cited by examiner

PRODUCING A HOLE IN A BIRD EGG FOR DETERMINING THE SEX OF THE BIRD EGG

The invention relates to a method for positioning a measuring point on at least one blood-carrying vessel of an opened bird egg to subsequently determine the sex of the bird egg.

Generally, according to FIG. 1, a chicken egg 1 comprises on incubation day 3.5 an egg shell 13, composed of a calcareous shell 14 with an adherent outer shell membrane 15 and inner shell membrane 16, an air space 17, an embryo 18 with extra-embryonic blood vessels 19, an egg white 20, and a yolk 21 that is surrounded by the yolk membrane 22. The egg shell 13 constitutes an important protective barrier for the egg 1 throughout the entire incubation. The calcareous shell 14 protects the egg contents against mechanical influences during the incubation period. Shell membranes bear against the inner side of the calcareous shell 14, which membranes are composed of the outer shell membrane 15 and the inner shell membrane 16. The shell membranes prevent the intrusion of microorganisms and regulate the milieu in the interior of the egg 1, for example, the fluid balance. Depending on the point in time at which the protective barrier is breached by what is referred to as a "windowing" of the egg shell 13 and how severely this takes place, the development of the embryo 18 and the hatching rates can be markedly influenced, wherein windowing is understood as meaning the creation of a hole 8 in the egg shell 13.

Thus, the hatching rate of non-incubated eggs decreases drastically after windowing through the entire egg shell, but removing only one calcareous shell window while preserving the shell membrane does not negatively affect the hatching rate, as is described in the publication J. Brake, et al.: Egg Handling and Storage, 1997, Poultry science 76; p. 144-151. According to the prior art, methods for determining the sex at a very early point in time of the incubation, that is, in a period between the start of incubation and incubation day seven before the sensitivity to pain begins, require a window 8 in the egg shell 13 in order to create access for optical measurements, as is described in the publications DE 10 2014 010 150 A1: Verfahren und Vorrichtung zur Ramanspektroskopischen in-ovo Geschlechtsbestimmung von befruchteten und bebrüteten Hühnereier, DE 10 2016 005 974.5: Verfahren und Vorrichtung zur Einstellung des Laserfokus eines Anregungslasers in blutdurchflossenen Gefäßen für optische Messungen zur Bestimmung des Geschlechtes von Vogeleiern, and DE 10 2016 004 051.3: Verfahren und Vorrichtung zur optischen in-ovo Geschlechtsbestimmung von befruchteten und bebrüteten Vogeleiern.

One disadvantage of the noted methods in the cited publications is that, depending on the point in time of the examination and on the hole size, the hatching rate in these methods can be negatively affected by the windowing where the window 8 is created both through the calcareous shell 14 and also through the two shell membranes 15, 16. If a laser is used according to the parameters specified in the publications cited above, this is the case at every location of the chicken egg 1.

In principle, the windowing can take place anywhere on the bird egg; preferably, it occurs at one end, on the pointed end.

In a commercial hatchery, the eggs are exclusively incubated according to FIG. 2 in a vertical position with the pointed end 3 facing downwards. The blunt end 2 is directed upwards, since otherwise no embryonic development takes place. When a hole 8 is created at the pointed end 3 according to FIG. 2b, the eggs 1 are turned 180° before the egg-opening and the subsequent determination of the sex. Because the external shell membrane 15 and calcareous shell 14 adhere to one another, creating a hole 8 at the pointed end 3 usually entails both the removal of the calcareous shell 14 and also in most cases the entire shell membrane 15, 16 within the set perforation. The partial or complete escape of air from the air cell 17 results, according to FIG. 2c, in a sinking of the egg contents, which necessitates a continuous tracking of the blood vessels 19 in the vertical Z direction of the egg axis 12 during the recording of the hack-scattered radiation. After the sex is determined, the eggs are closed and once again turned 180° according to FIG. 2d. FIGS. 2a, 2b, 2c, 2d show the conventional optical measurement at the pointed end 3 of an incubated chicken egg 1 and the necessary rotations 24 and 25. In FIG. 2b and FIG. 2c and FIG. 2d, the inner shell membrane 16 is broken or has been damaged, perforated and/or removed in the region of the hole. In FIG. 2d, a seal 29 has been affixed which closes the entire hole and the perforated shell membranes 15 and 16.

The disadvantage is the significant time delay caused by the required rotations until a measurement can be performed.

Thus, when the laser perforation is set at the pointed end 3 according to the prior art after a prior rotation of the egg 1, the embryo 18 is located directly beneath the egg shell 13, as is shown in FIG. 2b. Damage to the embryo 18 or the extra-embryonic blood vessels 19 caused by thermal damage during the creation of the laser perforation is not ruled out due to the variability of the calcareous shell thickness.

When an egg is opened at the pointed end 3, the gravity acting under ambient pressure (due to the mass of what is mostly egg yolk and egg white) on the air space 17 results in a partial or complete escape of air. This causes a vertical movement of the blood vessel 19 (Z direction/egg axis 12) on the order of the magnitude of the height of the air cell 17 before and/or during the recording of the back-scattered radiation. Since the blood vessel 19 irradiated with the laser radiation 30 can thereby move out of the laser focus, a vessel tracking is necessary.

It is therefore the object of the invention to specify a method for positioning a measuring point on at least one blood-carrying vessel of an opened bird egg to subsequently determine the sex of the bird egg, which method is suitably embodied so that at least rotations of the incubated eggs and a vessel tracking for an opened egg can be avoided.

The object is attained by the features of the independent patent claims, wherein the dependent patent claims recite advantageous embodiments of the invention.

In the method for positioning a measuring point on at least one blood-carrying vessel of an opened bird egg to subsequently determine the sex of the bird egg with a production of a hole on the bird egg that comprises at least a blunt end and a pointed end as well as an egg shell having an inner shell membrane and an outer shell membrane located more proximately to the calcareous shell of the bird egg, the bird egg is opened in order to perform at least one optical measurement related to the blood, wherein the production of the hole at the blunt end of the bird egg is carried out by means of a hole-producing unit, wherein the hole affects the calcareous shell and the outer shell membrane, which forms an air space with the inner shell membrane, and the inner shell membrane remains intact, wherein in the region of the hole at the blunt end beneath the intact inner shell membrane at least one blood vessel is registered and the blood is excited by means of a preset incident radiation, with the back-scattered radiation of the blood, which radiation is conducted through the intact inner shell membrane, being measured, detected and evaluated for determining the sex.

The calcareous shell and adherent outer shell membrane are thereby opened and the blood of at least the blood vessel 5 is spectroscopically examined, and the inner shell membrane remains intact during the spectroscopic optical measuring signal acquisition through at least the inner shell membrane of the egg shell.

Within the scope of the invention, the registering of a blood vessel is understood as meaning the locating and selecting of the at least one extra-embryonic or embryonic blood vessel in the opened egg, which blood vessel is intended for the excitation of the blood and the subsequent determination of the sex, wherein the focusing of the optical unit onto the registered blood vessel (focusing on the X, Y, Z plane) is also carried out during the registering of the blood vessel.

Before and during the measurement, a temperature control of the egg holder and measurement environment of the egg can be performed with an assigned unit for temperature control.

After the detection of the selected back-scattered radiation, the hole in the end is closed and the incubation of the egg for which the sex has been determined to be female is continued.

The following advantages result with the windowing at the blunt end of the egg in the region of the air cell:

If the vertical positioning of the egg used in all commercial hatcheries, with the blunt end directed upwards, is assumed, the egg is not turned or rotated before and after the sex determination.

Because of differences in density, the embryo, including the extra-embryonic blood vessels, is always located at the highest point of the egg interior, that is, in the region of the blunt end, on the first incubation days. When a laser perforation is set in a vertical incubation position, that is, with the blunt end facing upwards according to the invention, the embryo is located beneath the inner shell membrane. Between the calcareous shell and the inner shell membrane, the air cell ensures that the risk of damage to the embryo when the laser perforation is set is significantly reduced.

The egg-opening or the hole-production entails the removal of the calcareous shell and only the external shell membrane within the perforation; beneath the inner shell membrane, the embryo remains protected against external environmental influences and a potential contamination with germs. By means of this much less invasive method, a significant improvement in the hatching rate is achieved according to the invention.

The preservation of the entire inner shell membrane furthermore results in the preservation, to the greatest possible extent, of the positional relations of the egg yolk, egg white and air within the egg. During the incubation, a slight negative pressure forms in the egg.

When the egg is opened at the blunt end, a vertical movement of the blood vessels caused by the change in pressure does not occur, since there is no compressible air beneath the yolk and egg white. The change in the forces acting on the inner shell membrane during the change in pressure from a slight negative pressure to the ambient pressure when the egg hole is produced at the blunt end results in only a minimal change in the curvature of the inner shell membrane. This change in pressure causes the embryo and the extra-embryonic blood vessels to be reversibly fixed to the inner shell membrane for the duration of the recording of the back-scattered radiation, which prevents a horizontal movement of the blood vessels in the X, Y direction. The tracking of the blood vessels or objective lens (vessel tracking) both in a vertical and also in a horizontal direction is thus not required. A movement of the blood vessels out of the laser focus, which could be caused by a reduction in the volume of the egg interior, does not occur, since the egg is not exposed to any significant temperature decrease during the recording of the back-scattered radiation.

The apparatus according to the invention for positioning a measuring point on at least one blood-carrying vessel of an opened bird egg within an egg tray for subsequently determining the sex of the bird egg, with the aforementioned method being performed, comprises at least a hole-producing unit for producing a hole at the blunt end of the bird egg;

an optical measuring device for measuring the back-scattered radiation related to the blood;

two axes that can be rotated/tilted on an XY-plane, which axes are connected to the egg tray, wherein the axes are operated by rotation/tilt signals;

a motor-controlled tilting apparatus that is connected to the axes; and a central control unit that is connected to the motor-controlled tilting apparatus;

wherein the axes are rotated such that, if the embryo drifts out of the central egg axis, the drifting embryo is positioned in the proximate region of the egg axis in a centered manner and a minimum distance between the curvature of the inner shell membrane and the embryo is achieved.

The connections between the motor-controlled tilting apparatus and the axes are at least embodied by the lines, and the connections between the motor-controlled tilting apparatus and the central control unit are at least embodied by the lines.

Before the hole 4 is produced at the blunt end 2, the embryo 18 and the blood vessels 19, 5 can be centered. The density differences in the egg 1 on the first days of incubation result in the embryo 18, including the extra-embryonic blood vessels 19, always being located at the highest point of the egg interior, that is, in the region of the blunt end 2. This means that, for incubation in a vertical incubating position, as is applied in commercial hatcheries, the embryo 18 and the blood vessels 19 are located directly beneath the inner shell membrane 16 at the blunt end 2 of the egg 1, namely typically in the center of the egg 1, as is shown in FIG. 4c. In some cases, because of the natural variability of the eggs 1, the embryo 18 can, as is shown in FIG. 4a, assume a position that is slightly laterally displaced from the vertical egg axis 12, and is secured to the inner shell membrane 16 in this position by weak adhesive forces. The normal case is illustrated in FIG. 4c.

To increase the percentage of eggs in which the embryo 18 floats in a centered manner beneath the inner shell membrane 16, an embryo-centering unit 8 with a tilting apparatus 11 according to FIG. 6 is used according to the invention. It is thus achieved that, for each measurement in the sex determination, at least one blood vessel 19 is located with a largest possible diameter in the measuring field 23.

The extra-embryonic blood vessel network 19 on incubation day four represents an approximately circular area 23 as a measuring point, as is illustrated in FIG. 4b. In principle, the measurement can be performed in any blood vessel 19, 5, 18 from this circular area 23, but the signal intensity is greater in larger blood vessels 19 and the duration of the spectroscopic measurement related to the blood is therefore shorter. The extra-embryonic blood vessels 19 in the center, which means in direct connection with the embryonic bloodstream, have the largest diameter. By contrast, the diameter of the more finely branched blood vessels 5 in the vicinity of the sinus terminalis is smaller.

The centering of the embryo 18 preferably takes place before the shell window is produced at the blunt end 2 of the egg 1, since the embryo 18 and the extra-embryonic blood vessels 19 weakly adhere to the inner shell membrane 16 after the opening 4, wherein this adhesion is reversible.

In the apparatus 37 according to the invention with the centering control unit/central control unit/embryo-centering unit 9 and tilting apparatus 11, the eggs 1 are, individually or in an egg tray 10, respectively tilted or tilt-rotated in the X and Y direction by a movement at an angle of at least 10° to 90°, preferably between 30°-60°, wherein an egg tray 10 is understood as meaning the often multiple 20-fold to 50-fold egg holders 6 used in the incubators in commercial hatcheries. The throughput speed for the tray 10 and the adjustable tilt angle are set such that the embryonic development is not negatively affected.

The creation of a hole 4 in the calcareous shell 14 of the bird egg 1 takes place by means of a hole-producing unit 39, preferably with a laser, and according to the invention at the blunt end 2 with a diameter of 3 mm to 18 mm, preferably between 8 mm and 15 mm.

A vessel detection can occur by means of an optical unit for focusing in a single blood vessel (focusing on an X, Y, Z plane) through the inner shell membrane 16. However, the transparency of the inner shell membrane 16 manifests itself in the variable bird eggs, also depending on the breed, with varying degrees of intensity.

It was therefore possible to discover that, for determining the sex of the bird eggs, it is necessary to use not only the flow movement of the erythrocytes as a focusing indicator for the detection of the blood vessels, but rather according to the invention to use additional optical signals, such as intensity-related measuring signals or optical coherence tomography (OCT) signals, for example. For this reason, according to the invention, the excitation of the blood is achieved through incident radiation 30 and the recording of the back-scattered radiation (Raman radiation 27 and/or fluorescence radiation 28) is achieved using an optical unit.

The registering of the blood vessels and the optical excitation of the blood are achieved in that the focus of the incident excitation radiation is positioned in a blood vessel and a signal generated by a laser is used. This signal is preferably so focused that the dimension of the laser spot is comparable or less than the diameter of the blood vessels. The laser wavelength is selected such that the excitation of the incident radiation produces a signal from the blood, which signal is spectrally shifted from the excitation laser wavelength.

The intensity of the back-scattered radiation is measured in the subrange of the spectrum that contains blood-specific information. The signal obtained from the blood in the vessels thereby differs, in terminals of the intensity and/or the spectral properties, from signals which are obtained from egg structures outside of the blood vessels.

The correct focus position corresponds to the coordinates at which the intensity signal reaches a maximum. The intensity of the fluorescence or the intensity and the profile of a Raman band, or the intensities and profiles of multiple Raman bands of a blood component can thereby form the blood-specific intensity-related signal, which according to the invention is used for focus-finding through the inner shell membrane. The laser, the focus of which is used for positioning, can be the same laser that is also used for exciting the sex-specific Raman and/or fluorescence signal. The laser that is used for positioning the laser focus in the blood vessel can also be a laser different from the excitation of the sex-specific signal that is only used for the purpose of positioning the laser focus. In this case, the positioning laser is selected such that a very high-intensity, blood-specific (but not necessarily sex-specific) signal is produced, which signal can be recorded using simple, economical and fast detection systems. It is also possible to use a positioning laser, which is significantly more inexpensive compared to laser sources that are used to excite the sex-specific signal of the blood.

It should thereby be taken into consideration not only that the limited transparency of the inner shell membrane requires an adaptation, according to the invention, of the method for positioning the laser focus in the blood vessel, but that the intensity of the sex-specific signal that is acquired for determining the sex of the eggs is also influenced.

The inner shell membrane of the egg is an inhomogeneous medium which scatters both the incident laser radiation and also the generated sex-specific signal that is emitted by the blood. To allow the variations in the transparency of the inner shell membrane between the eggs to be corrected, a parameter must be used with which the intensity of the sex-specific signals is corrected and the intensity loss due to the reduced membrane transparency compensated for.

It is possible that multiple lasers are used for the registering of the blood vessels and the excitation of the blood. For example, one laser for exciting sex-specific Raman and fluorescence signals in the range between 790 nm and 1050 nm can be used, while a second green or blue laser is used to excite an intense blood-specific hemoglobin fluorescence between 550 nm and 750 nm. The intensity of this fluorescence can be measured with photodiodes and used to position the laser focus in the blood vessel.

The advantages of the method according to the invention are as follows:

Chicken eggs are incubated exclusively in a vertical position in commercial hatcheries. Traditionally, the pointed end must thereby be positioned facing downwards, since otherwise no embryonic development occurs. A spectroscopic sex determination at the pointed end therefore requires that the eggs be turned twice; before and after the spectroscopic sex determination (as shown in FIGS. 2a, 2b, 2c, 2d). In the sex determination according to the invention at the blunt end 2, however, this double turning is no longer required, which proves beneficial for the embryonic development.

In the opening of the eggs at the pointed end 3 known from the prior art, a partial or complete escape of air from the air cell results from the pressure differences in the egg 1, which causes a vertical movement of the blood vessels. However; with the preservation of the inner shell membrane 16 according to the invention, the blood vessels 5, 18, 19 are secured.

The air space 17 is located between the embryo 18 and the egg shell 13 in the region of the laser perforation. Thus, according to the invention, the risk of damage to the embryo 18 and/or to the extra-embryonic blood vessels 19 is reduced during the setting of the laser perforation and the lifting-off of the shell cap from the remaining part of the egg 1.

A major advantage of the method according to the invention is that a spectroscopic sex determination is rendered possible under minimally invasive conditions at a very early point in time of the incubation. In this manner, it is achieved that the hatching rates remain unaffected.

With regard to the apparatus according to the invention, the egg tray 10 is mounted by means of two rotation/tilt axes 33 and 36 arranged perpendicularly to one another. The rotation/tilt axes 33 and 36 are supplied with rotation/tilt signals via the corresponding lines 31 and 32. A central control unit or embryo-centering unit 9 supplies the motor-controlled tilting apparatus 11 with rotation/tilt signals, which it passes along to the axes 33 and 36.

The apparatus 37 for positioning a measuring point 23 on at least one blood-carrying vessel 5, 18, 19 of an opened bird egg 1 within an egg tray 10 for subsequently determining the sex of the bird egg 1 comprises at least a hole-producing unit 39, or hole-producer, for producing a hole (4) at the blunt end (2) of the bird egg (1); an optical measuring device for measuring the back-scattered radiation (26) related to the blood; two axes 33, 36 that can be rotated/tilted on an XY-plane, which axes are connected to the egg tray 10, wherein the axes 33, 36 are operated by rotation/tilt signals; a motor-controlled tilting apparatus 11 that is connected to the axes 33, 36; and a central control unit 9 that is connected to the motor-controlled tilting apparatus 11, wherein the axes 33, 36 are rotated such that, if the embryo 18 drifts out of the central egg axis 12, the drifting embryo 18 is positioned in the proximate region of the egg axis 12 in a centered manner and a minimum distance between the curvature 38 of the inner shell membrane 16 and the embryo is achieved.

The connections between the motor-controlled tilting apparatus 11 and the axes 33 and 36 are embodied by the lines 31, 32, and the connections between the motor-controlled tilting apparatus 11 and the central control unit 9 are embodied by the lines 34, 35.

The hole-producing unit is adjusted to the perforation of the egg cap in such a way that, during the perforation and during the subsequent lifting-off of the shell cap for the formation of the hole 8, the inner shell membrane 16 is not damaged.

The invention is explained by means of two exemplary embodiments with the aid of drawings.

In this matter:

FIG. 1 shows a schematic illustration of the structure of a chicken egg on incubation day 3.5 according to the prior art;

FIG. 2 shows schematic illustrations of the sequence of steps for performing a measurement at the pointed end of a chicken egg according to the prior art, wherein FIG. 2a shows an incubation position, FIG. 2b shows an egg-opening through the calcareous shell and through outer shell membranes and inner shell membranes, FIG. 2c shows a measurement of embryonic or extra-embryonic blood vessels through the egg white layer, and FIG. 2d shows the re-formation of the air cell in the incubation position within three days;

Figure 1:
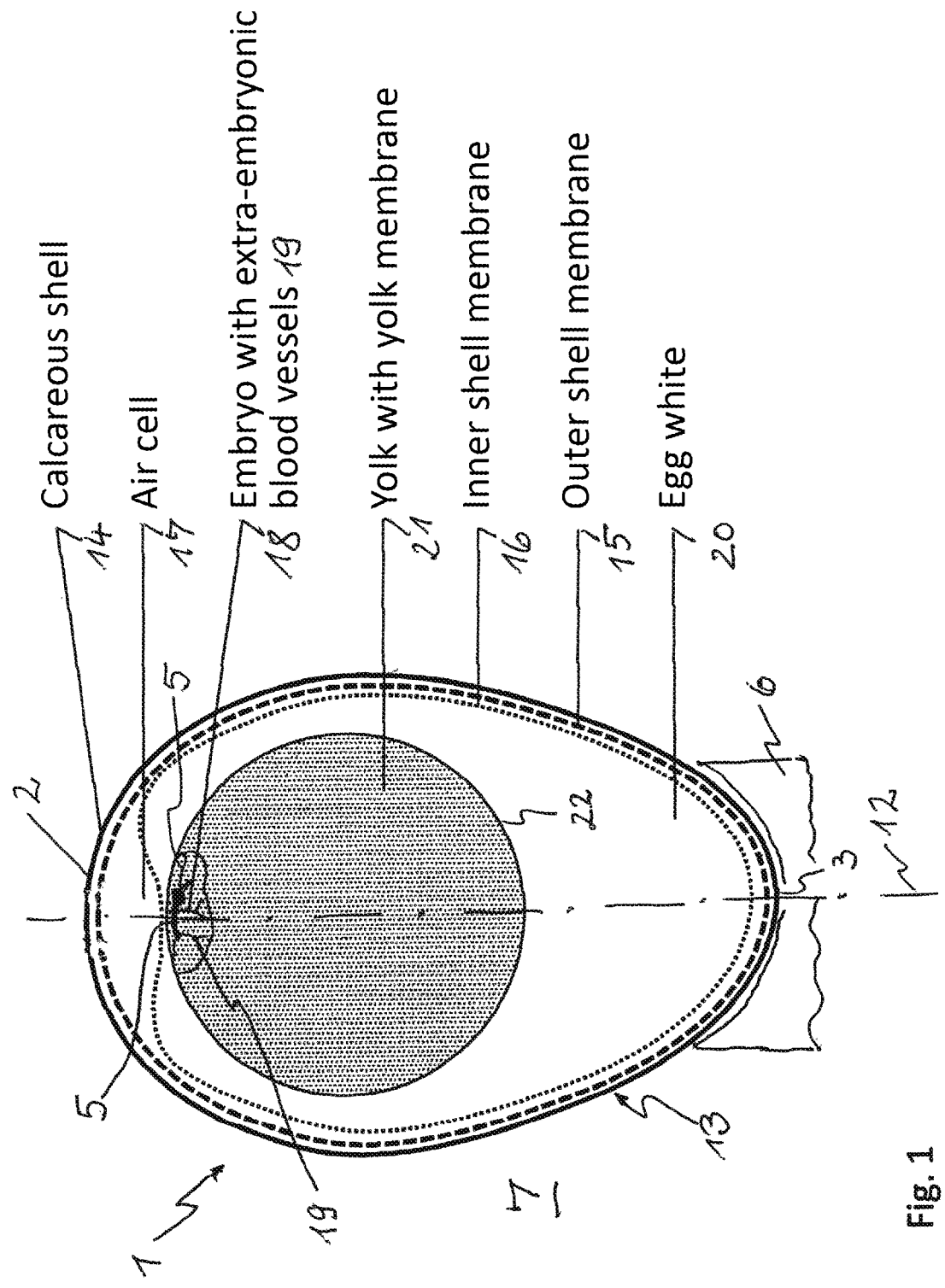
Figures 2A, 2B, 2C, 2D:
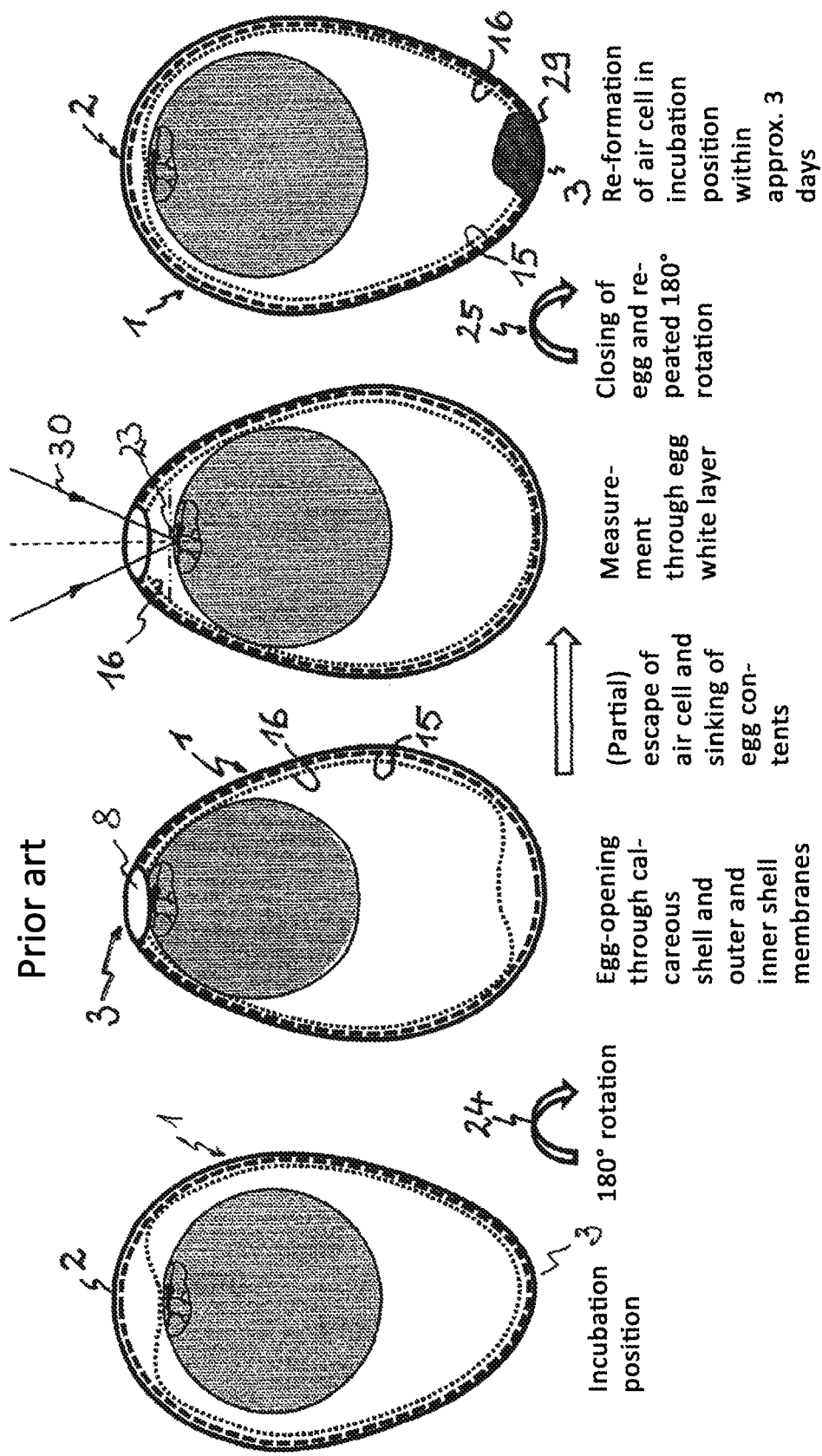
Figures 3A, 3B, 4:
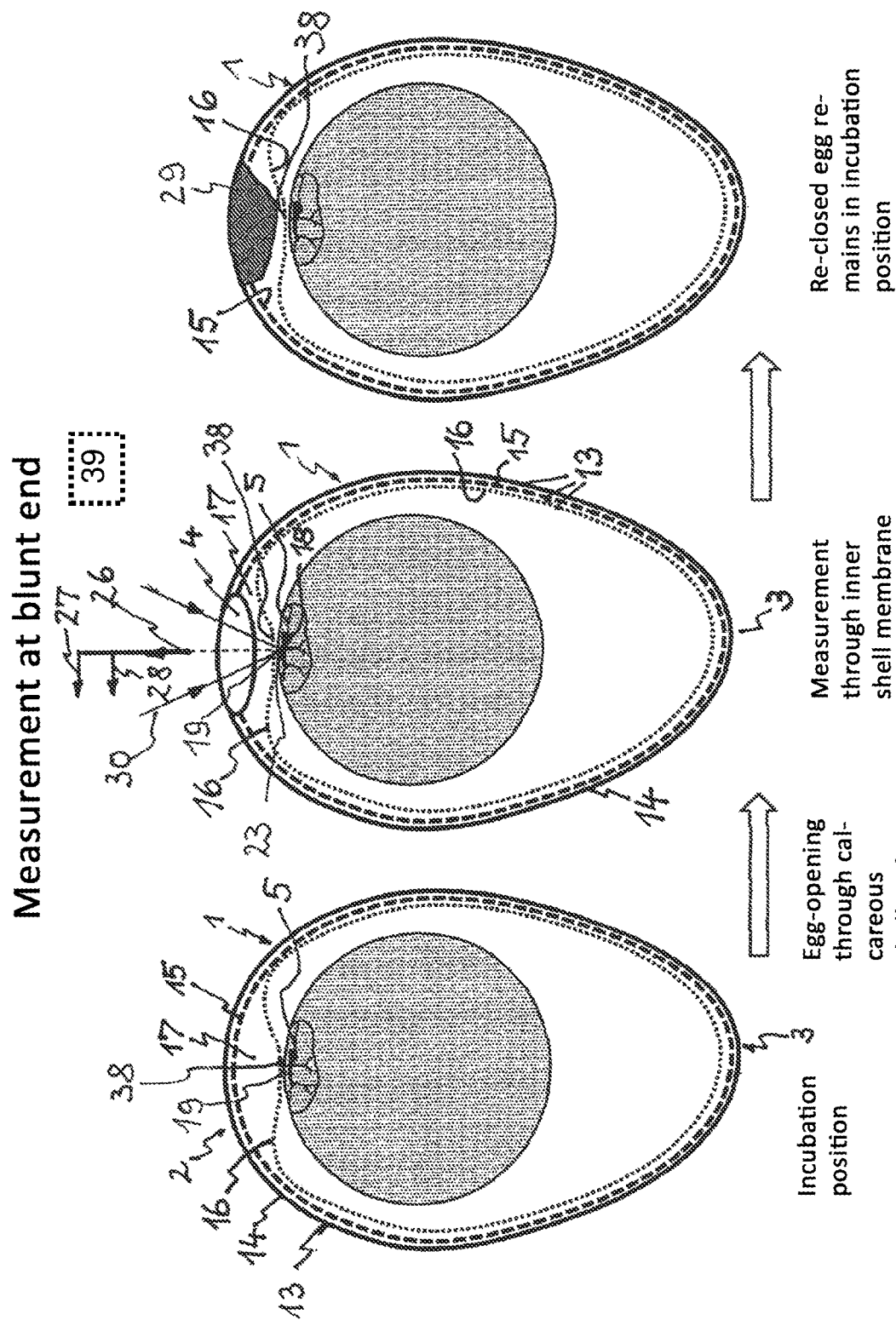
FIG. 3a shows an incubation position for the subsequent performance of a measurement at the blunt end of a chicken egg.
FIG. 3b shows a chicken egg that has been closed again and has been determined to be female, which egg remains in the incubation position.
FIG. 4 shows an egg-opening through the calcareous shell and outer shell membrane, with an optical blood-related measurement through the intact inner shell membrane, wherein the blood of a blood vessel located directly beneath the inner shell membrane is measured.
Figure 4C:
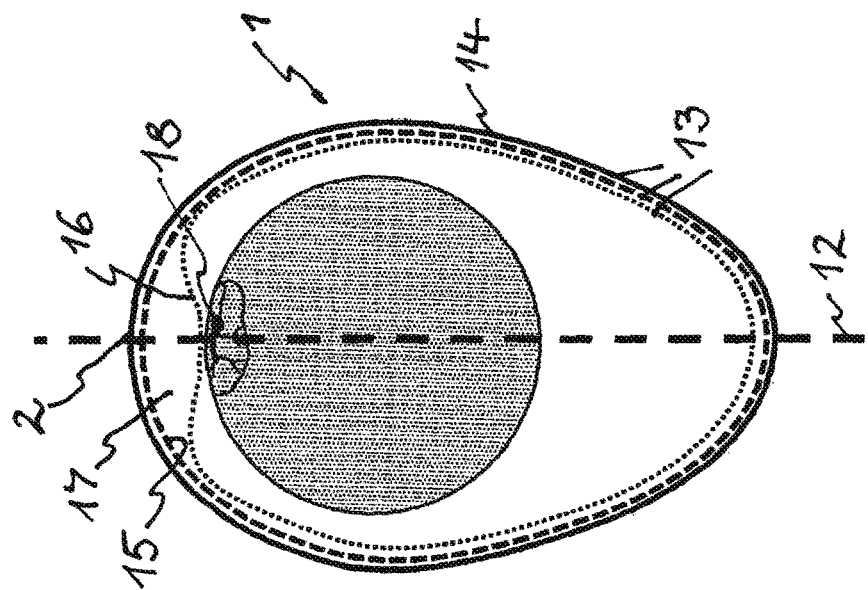
FIG. 4c shows a schematic illustration of an egg, showing a securing of the embryonic network to the inner shell membrane in position with the vertical egg axis through weak adhesive forces.
Figure 4A:
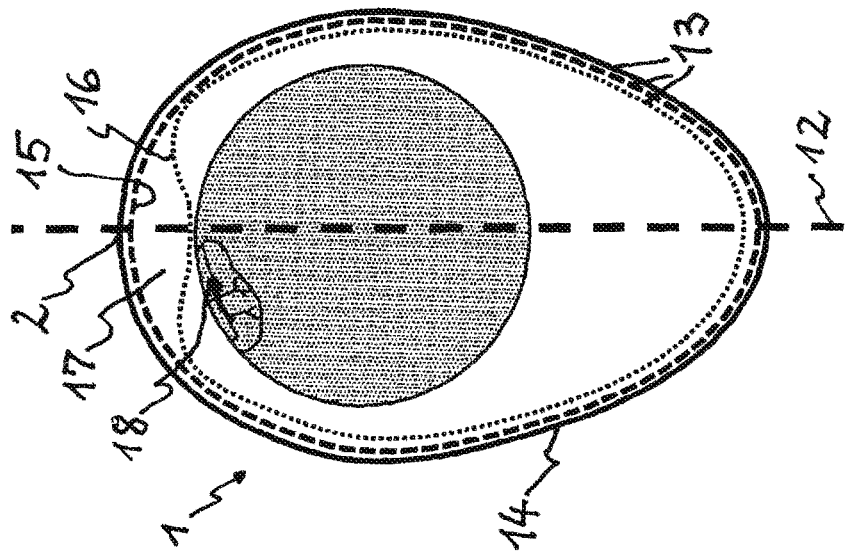
FIG. 4a shows a schematic illustration of an egg, showing the natural variability of the eggs with a position slightly laterally displaced from the vertical egg axis.
Figure 4B:
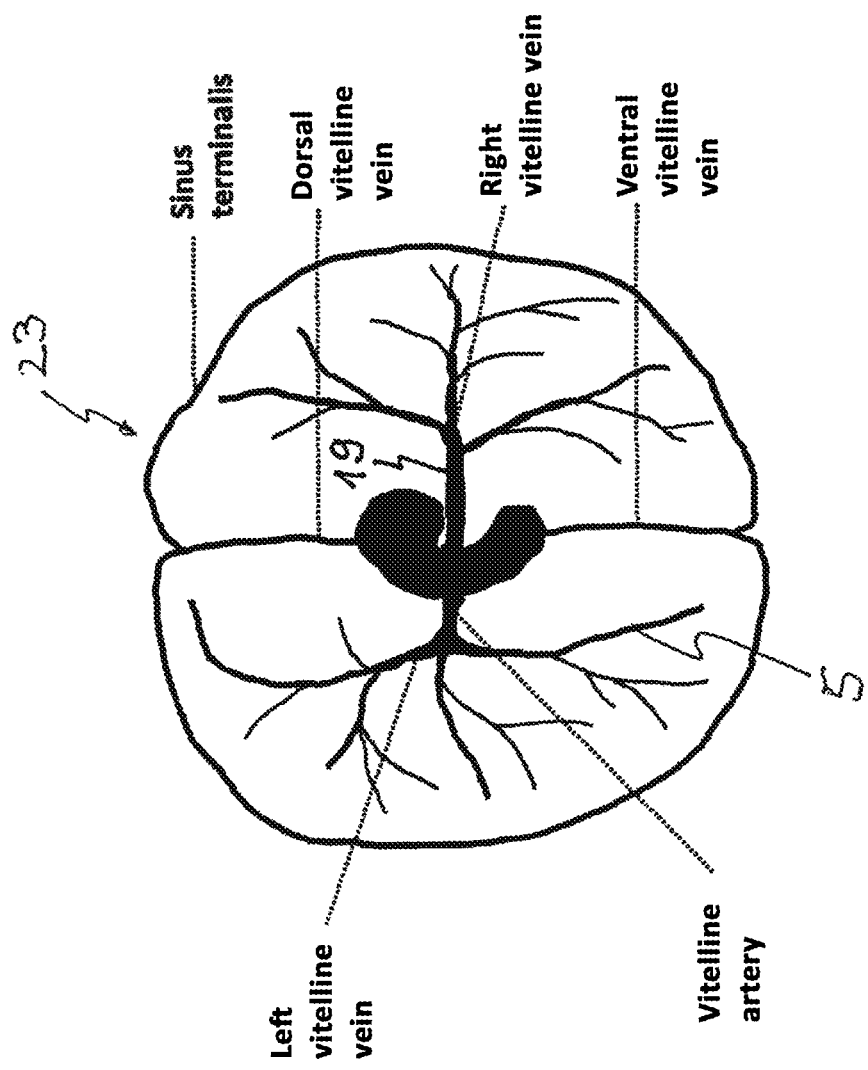
FIG. 4b shows an extra-embryonic blood vessel network on incubation day four in the form of an approximately circular area.
Figure 5:
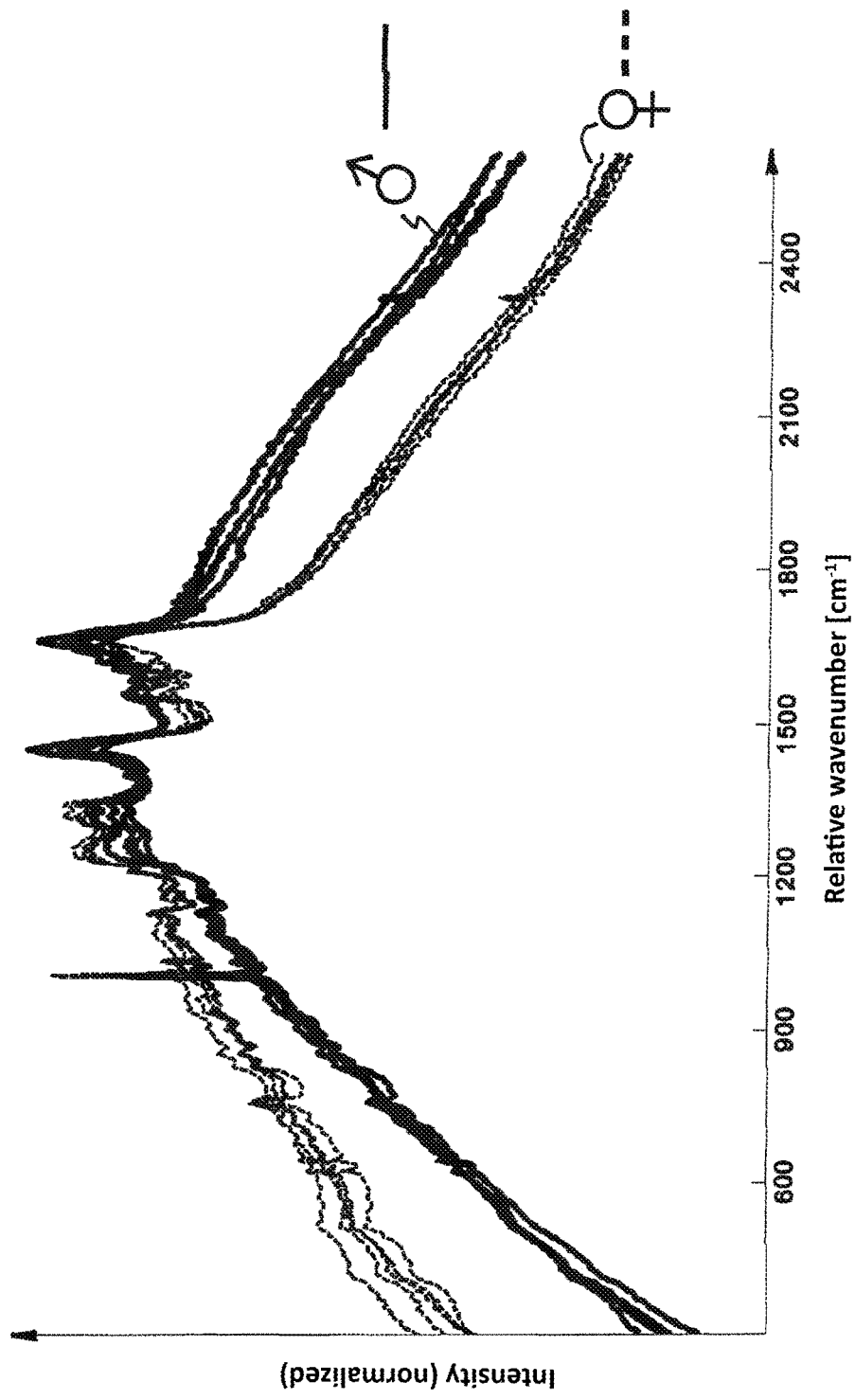
Figure 6:
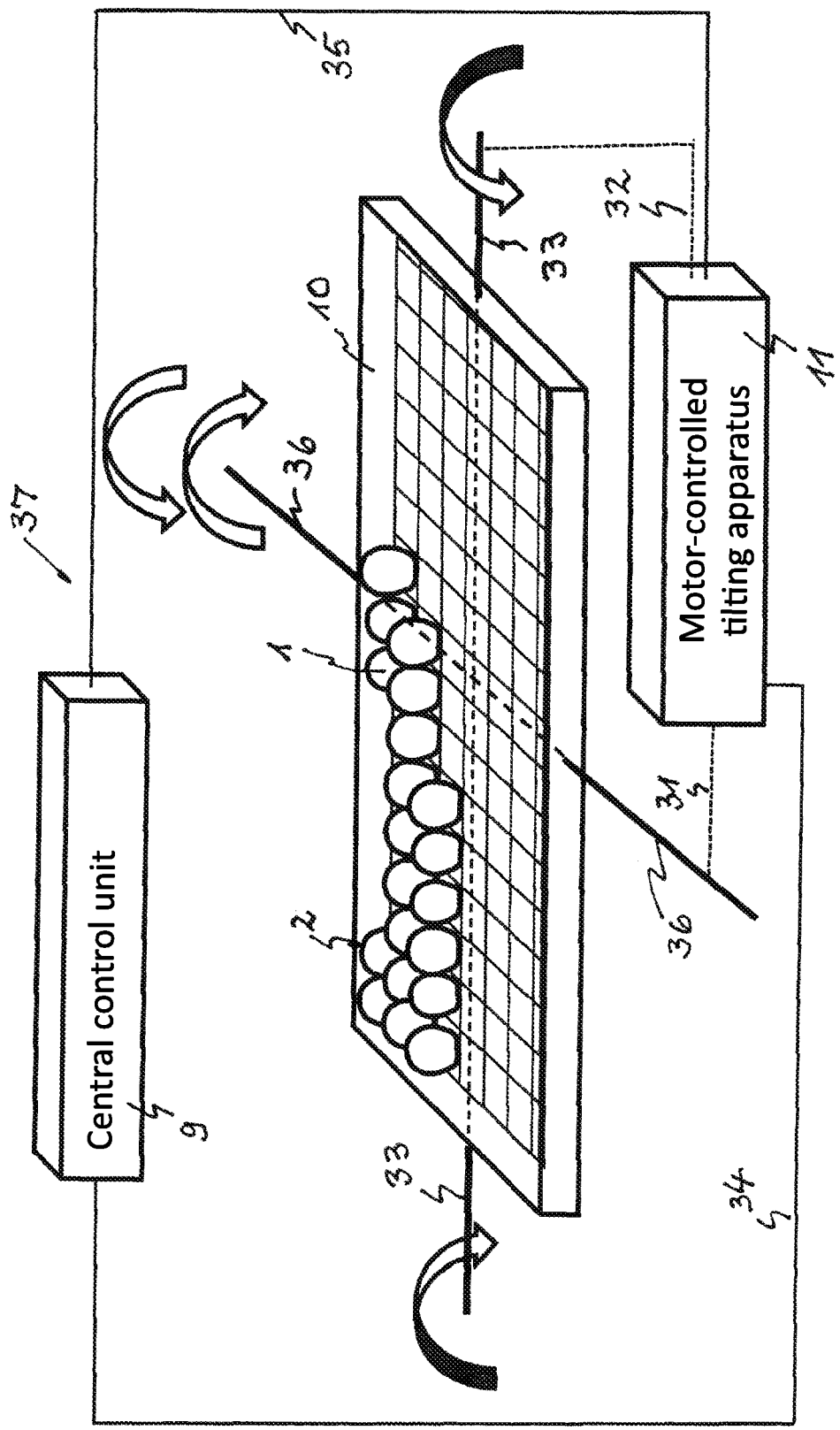

FIG. 5 shows two evaluated intensity(-normalized)/relative wavenumber curves, for example, for five chicken eggs with a sex of male (solid line) and for five chicken eggs with a sex of female (dashed line) following an optical measurement of the back-scattered radiation of the blood through the intact inner shell membrane; and FIG. 6 shows a schematic illustration of an egg tray in connection with a tilting apparatus for tilting about at least two set axes, and with a central control unit.

EXEMPLARY EMBODIMENT 1

The embryo 18, which is freely movable in the unopened egg, is centered beneath the inner shell membrane 16 by a bird egg 1 being tipped twice at an angle of about 40° in the X and Y direction. An opening with a diameter of 15 mm is created at the blunt end 2 on incubation day 3.5. An extra-embryonic blood vessel 19 is selected through the inner shell membrane 16 using green LED illumination with a spectral range of 500 nm-550 nm and by means of a camera. A CW laser beam 30 from the laser beam source (output: 200 mW; $\lambda=785$ nm) is focused onto the extra-embryonic blood vessel 19 by means of an objective lens and the blood is excited.

The recording of the back-scattered radiation 26, including the fluorescence radiation 28, and the evaluation in an evaluation unit are then carried out. Vector normalization, in which a normalization of the intensity in relation to the relative wavenumber is conducted, is used as the method performed for preprocessing the recorded spectra for the sex determination (FIG. 5).

In addition, the egg holder 6 and the measurement environment 7 are temperature controlled in order to prevent the wrinkling of the inner shell membrane 16 during the egg-opening, and to thus minimize signal losses due to a scattering of the back-scattered radiation 26 at the inner shell membrane 16. With the temperature control, a minimal defocusing of the blood vessels 19 due to a reduction in volume caused by the cooling egg contents during the measurement of the back-scattered radiation 26 at the opened blunt end 2 of the egg 1 is avoided. For this purpose, a unit for controlling the temperature (not shown) with a temperature-setting control unit for the eggs 1 being examined is used, with which unit a preset constant temperature is programmed to avoid a wrinkling of the inner shell membrane 16.

After the sex is determined, the hole 4 in the blunt end 2 is closed by means of a seal 29, and the incubation of the egg 1 that has been determined to be female is continued.

EXEMPLARY EMBODIMENT 2

The embryo 18, which is freely movable in the unopened egg, is centered beneath the inner shell membrane 16 by a bird egg 1 being tipped twice at an angle of 40° in the X and Y direction. An opening with a diameter of 10 mm is created at the blunt end 2 on incubation day 3.5. The hole 4 at the blunt end 2 of the bird egg 1 is produced by means of a hole-producing unit (not illustrated), wherein the hole 4 affects the calcareous shell 14 and the outer shell membrane 15, which forms an air space 17 with an inner shell membrane 16, and the inner shell membrane 16 remains intact.

Then, in the region of the hole 4 at the blunt end 2 beneath the intact inner shell membrane 16, at least one blood vessel 5 is registered and the blood therein is excited by means of a preset incident radiation 30; the back-scattered radiation 26 conducted through the intact inner shell membrane 16 is measured; the blood, at least of the blood vessel 5, is spectroscopically examined and detected and evaluated for a sex determination; wherein before and during the measurement, a temperature control of the egg holder 6 and the measurement environment 7 of the egg 1 is carried out with an assigned temperature-control unit in order to avoid a differing and drastic cooling after the removal from the incubator. The registering of the blood vessel and excitation of the blood is achieved by a laser having an excitation wavelength of 785 nm. The fluorescence signal in the range of 790-1050 nm is generated by the hemoglobin in the blood and is therefore blood-specific. The positioning of the laser focus in the blood vessel takes place based on the maximization of the fluorescence intensity, which is measured using the spectrometer for the determination of the sex.

After the focus is positioned in the blood vessel, the measurement of the sex-specific parameters takes place with a spectrometer. The data processing and evaluation of the membrane-corrected, sex-specific signals then occurs.

After the detection of the selected back-scattered radiation 26, the hole 4 in the end 2 is closed with a seal 29, and the incubation of the egg 1 that has been determined to be female is continued, while the egg that has been determined to be male is separated out of the incubating tray 10.

LIST OF REFERENCE NUMERALS

1 Bird egg
2 Blunt end
3 Pointed end
4 Hole in the blunt end
5 Blood vessel
6 Egg holder
7 Measurement environment
8 Hole at the pointed end
9 Embryo-centering unit/central control unit/centering control unit
10 Egg tray
11 Tilting apparatus
12 Vertical axis in the egg
13 Egg shell
14 Calcareous shell
15 Outer shell membrane
16 Inner shell membrane
17 Air space/air cell
18 Embryo
19 Extra-embryonic blood vessels
20 Egg white
21 Yoke
22 Yoke membrane
23 Measuring point/measuring area
24 First rotation
25 Second rotation
26 Back-scattered radiation
27 Raman radiation
28 Fluorescence radiation
29 Seal
30 Preset incident radiation
31 Line
32 Line
33 First rotation/tilt axis
34 Line
35 Line
36 Second rotation/tilt axis
37 Apparatus
38 Curvature
39 Hole-producing unit

The invention claimed is:

1. A method for positioning a measuring point on at least one blood-carrying vessel of an opened bird egg to subsequently determine the sex of the bird egg, with a production of a hole on the bird egg, which comprises at least a blunt end and a pointed end as well as an egg shell having an inner shell membrane and an outer shell membrane located more proximately to the calcareous shell of the bird egg, wherein the bird egg is opened in order to perform at least one optical measurement related to the blood, the method comprising:

carrying out the production of the hole at the blunt end of the bird egg by means of a hole producer, wherein the hole affects the calcareous shell and the outer shell membrane, which forms an air space with an inner shell membrane, and the inner shell membrane remains intact, wherein in the region of the hole at the blunt end beneath the intact inner shell membrane at least one blood vessel is registered and the blood therein is excited by means of a preset incident radiation, with the back-scattered radiation of the blood by which radiation is conducted through the intact inner shell membrane and is related to the blood, being measured, detected and evaluated for determining the sex;

twisting shafts that are rotatable/tiltable in an xy-plane by means of a motor-controlled tilt apparatus, which is connected to a central controller, so that should the position of the embryo deviate from the central egg axis the deviating position of the embryo is brought into the immediate region of the egg axis in a centered fashion and a minimum distance is obtained between the arch of the inner shell membrane and the embryo.

2. The method according to claim 1, wherein:
during the egg-opening, the calcareous shell provided with the adherent outer shell membrane, is perforated and the blood of at least one blood vessel is spectroscopically examined, and the inner shell membrane remains intact during the egg-opening and the subsequent spectroscopic optical measuring signal acquisition through at least the inner shell membrane of the egg shell.

3. The method according to claim 1, wherein:
before and during the measurement, a temperature control of the egg holder and the measurement environment of the egg are performed with an assigned temperature controller.

4. The method according to claim 1, wherein:
after the detection of the back-scattered radiation, the hole in the blunt end is closed by means of a seal, and at least the incubation of the egg for which the sex has been determined to be female is continued.

5. The method according to claim 1, wherein:
one or more lasers are used for registering a blood vessel, for optical excitations of the blood and/or for measurement of the back-scattered radiation related to the blood.

6. An apparatus for positioning a measuring point on at least one blood-carrying vessel of an opened bird egg within an egg tray for subsequently determining the sex of the bird egg, the apparatus comprising at least:
- a hole producer configured to produce a hole at the blunt end of the bird egg;
- an optical measurer configured to measure the backscattered radiation related to the blood;
- two axes that can be rotated/tilted on an xy-plane, which axes are connected to the egg tray, wherein the axes are operated by rotation/tilt signals;
- a motor-controlled tilting apparatus that is connected to the axes; and
- a central controller that is connected to the motor-controlled tilting apparatus;
- wherein the central controller is configured to rotate the axes such that, if the embryo drifts out of the central egg axis, the drifting embryo is positioned in the proximate region of the egg axis in a centered manner and a minimum distance between the curvature of the inner shell membrane and the embryo is achieved.

7. The apparatus according to claim 6, wherein:
the connections between the motor-controlled tilting apparatus and the axes are at least embodied by connection lines, and the connections between the motor-controlled tilting apparatus and the central controller are at least embodied by connection lines.

* * * * *